United States Patent [19]

Tama

[11] 4,418,697

[45] Dec. 6, 1983

[54] ELECTRODE ATTACHMENT METHOD

[76] Inventor: Francine Tama, 48 E. Riding Dr., Cherry Hill, N.J. 08003

[21] Appl. No.: 293,518

[22] Filed: Aug. 17, 1981

[51] Int. Cl.³ .............................................. A61B 5/04
[52] U.S. Cl. .................................... 128/640; 128/802
[58] Field of Search .............................. 128/639–641, 128/798, 791–793, 802, 803

[56] References Cited

U.S. PATENT DOCUMENTS

| 2,872,926 | 2/1959 | Aldeman | 128/640 |
| 3,426,746 | 2/1969 | Seamans, Jr. | 128/640 |
| 3,528,408 | 9/1970 | Opperman | 128/640 |
| 3,545,432 | 12/1970 | Berman | 128/640 |

OTHER PUBLICATIONS

Gilson et al., "Continuous Electrocardiograms", The Am. J. of Cardiology, pp. 212–215, Aug. 1961.
2 Page Pamphlet, "Facts/Things of Interest".
"The Toy with One Moving Part", pp. 71–79.
Albin et al., "Electrode Fixation . . . ", EEG & Clin. Neuro., 1964, 17:696–697.

*Primary Examiner*—Lee S. Cohen
*Attorney, Agent, or Firm*—Weiser & Stapler

[57] ABSTRACT

A method of securing an electrode to the skin of a human body for treatment or diagnostic purposes includes the steps of positioning a surface of the electrode in contact with a desired skin area from which, or into which electrical energy is to be directed, and maintaining the electrode in its desired position by confining it within the periphery of a pliable, moldable and stretchable adhesive material conforming to the configuration of the electrode and having a peripheral region surrounding the periphery of the electrode and being secured to the skin. Preferably the electrode surface is adhered to the skin without interposing an adhesive polymer or an adhesive gel between them, and most preferably the pliable adhesive material is a putty including a silicone polymer.

4 Claims, 2 Drawing Figures

ELECTRODE ATTACHMENT METHOD

TECHNICAL FIELD

This invention relates generally to the field of electrical treatment and diagnostic devices, and more specifically to a method of attaching an electrode to the skin of a human body.

BACKGROUND ART

Electrical treatment and diagnostic techniques are well-established in the medical field. For example, it has become well recognized that electrical impulses can be employed for desired medical theraputic and physical rehabilitative purposes, such as in the treatment of paralytic, palsy and neurotic conditions. In certain applications, such as in electrolysis or in metallic ionization, it is desirable to place the bare metal electrode in contact with the user's skin. For other applications, and in particular when low-tension currents are used, the metal electrodes are conventionally covered with gauze or other absorbent material to prevent direct contact of the electrode with the patient's skin.

Regardless of the type of treatment desired, it is necessary to establish effective electrical communication between the electrode and the skin while maintaining the electrode in its desired position. A well-known technique for securing an electrode to the skin is to employ an electrode gel or adhesive between them. The following patents are representative of this technique: U.S. Pat. Nos. 3,989,050 (Buchalter); 4,248,247 (Ware et al); 4,008,721 (Burton); 4,166,453 (McClelland) and 4,243,051 (Wittemann).

Electrode gels and adhesives are often quite messy to use, and for many applications, do not provide the necessary retaining force to properly secure the electrode in its desired position. Moreover, for applications in which direct contact between the metal electrode and skin is desired, electrode gels and adhesives cannot be employed, and therefore, an alternative system needs to be used. In fact, even when gels and adhesives are to be used it is often desirable to more firmly retain the electrode to the skin; particularly when the user is going to be treated or monitored while in a relatively active state.

SUMMARY OF THE INVENTION

A method of securing an electrode to the skin of a human body for medical treatment or diagnostic purposes is accomplished by positioning the electrode in contact with a desired skin area from which, or into which electrical energy is to be directed; and maintaining the electrode in its desired position by confining it within the periphery of a pliable, moldable and stretchable adhesive material conforming to the configuration of the electrode and having a peripheral margin surrounding the periphery of the electrode and being secured directly to the skin.

Preferably the pliable material employed in this invention is a putty, and most preferably a putty formed of a silicone polymer. One suitable material utilized in this invention is Dow Corning 3179 dilatant compound, manufactured by Dow Corning Corp of Midland, Mich.

The preferred putties are organosiloxane-boron compounds constituting the heat reaction product of dimethyl silicone oil and boron; employing heat as the catalyst. Compounds of the general type utilized in this invention are disclosed in U.S. Pat. Nos. 2,431,878 (Gregor et al); 2,541,851 (Wright); 2,644,805 (Martin) and 3,350,344 (Beers). All of these latter-mentioned patents are incorporated herein by reference.

It should be understood that other pliable, moldable and stretchable adhesive materials can be employed; provided they do not interfere with the electrical characteristics of the system, and otherwise are capable of retaining the electrode in its desired intimate contact with the user's skin.

In accordance with the most preferred embodiment of this invention the pliable material is stretched or squeezed about an electrical conductor interconnecting the desired treatment or diagnostic equipment with the electrode. In other words, even the presence of the conductor connected to the electrode does not interfere with the ability of establishing and maintaining intimate engagement of the electrode with the skin.

The benefits of this invention are most significant when adhesive polymers or gels cannot be employed to assist in securing the electrode of the skin surface.

Other objects and advantages of this invention will be better understood by referring to the Description of the Preferred Embodiment of the Invention, taken in conjunction with the drawings.

DESCRIPTION OF THE PREFERRED EMBODIMENT OF THE INVENTION

Figure 2:
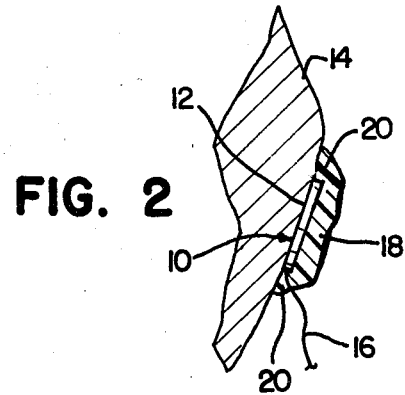
FIG. 2 is a sectional view taken through the electrode of FIG. 1.

Referring specifically to FIG. 2, the electrode 10 has its active surface 12 in intimate engagement with skin surface 14. In the illustrated embodiment the skin surface is in the region of the cheek muscle, and an electrical conductor 16 interconnects suitable treatment equipment (not shown) with the electrode 10 to introduce electrical current into the cheek muscle for the purpose of stimulating its contraction.

In accordance with this invention the electrode 10 is maintained in its desired position in close conformance with the skin surface by confining it within the periphery of a pliable, moldable and stretchable adhesive material 18. This material preferably is a putty-like substance, and can be squeezed about the electrode 10 so that it closely conforms to the electrode's configuration and completely surrounds the periphery thereof. The close conformance of the putty-like material 18 with the electrode 10 can be seen best in FIG. 2, and the manner in which it completely surrounds the electrode can be seen best in FIG. 1.

Figure 1:
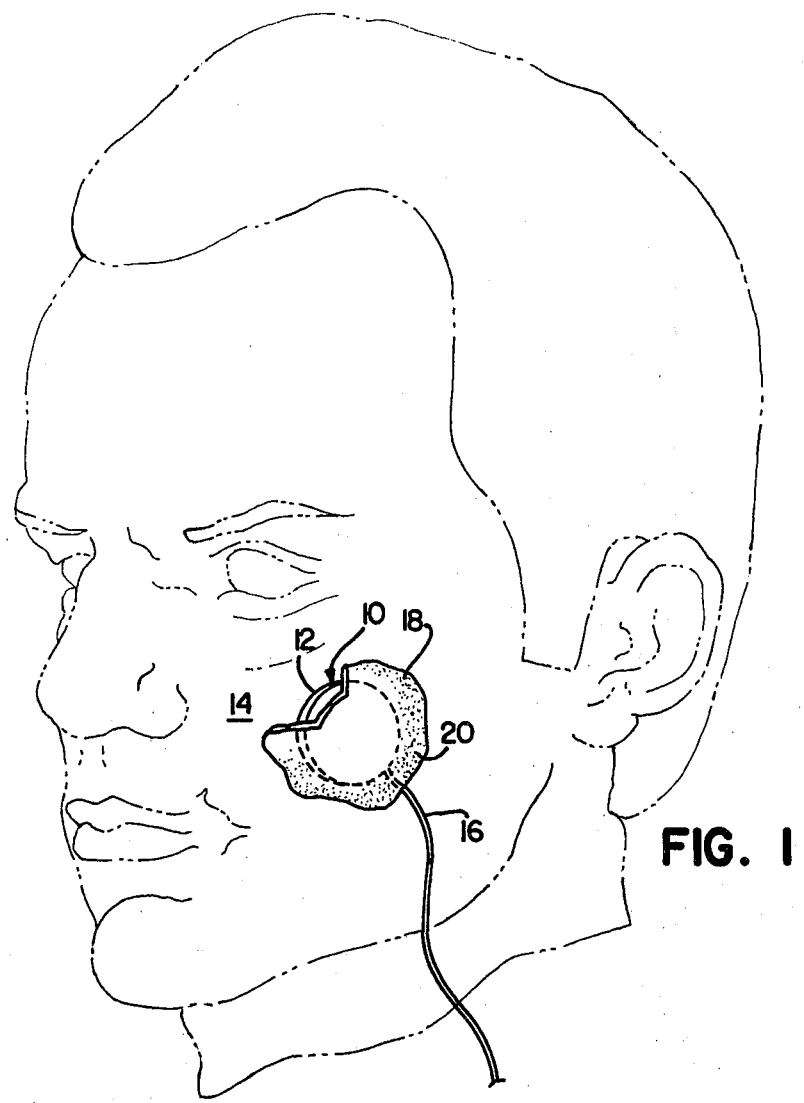
FIG. 1 is an isometric view illustrating the manner in which an electrode is maintained in proper position on the skin of a human body.

Referring to both FIGS. 1 and 2 the pliable material 18 includes a peripheral region 20 completely surrounding the periphery of the electrode and being directly adhered to the skin surface 14. The close conformity established between the pliable material 18 and the electrode 10, in conjunction with establishing adhesive engagement with the skin surface 14 about the entire periphery of the electrode, provides an extremely reliable and positive system for maintaining the electrode 10 in its desired position.

It should be noted that despite the presence of the conductor 16, the pliable material 18 is still capable of being adhesively attached to the skin surface 14 about the entire periphery of the electrode 10. This is a very desirable feature of the invention, and could not be achieved if it were not for the pliable, moldable and stretchable properties of the adhesive material 18.

As indicated earlier, the adhesive material 18 preferably is a silicone polymer putty, and most preferably is an organosiloxane-boron compound constituting the heat reaction product of dimethyl silicone oil and boron, utilizing heat as a catalyst. However, other pliable, moldable and stretchable adhesive materials can be employed provided they are capable of being squeezed, stretched or otherwise molded into close conformity with the general configuration with the electrode 10, and also are capable of being adhesively secured to the skin surface about the periphery of said electrode without interfering with the electrical treatment or diagnostic technique.

Although the present invention has been described with reference to the particular embodiments herein set forth, it is understood that the present disclosure has been made only by way of example and that numerous changes in the details of construction may be resorted to without departing from the spirit and scope of the invention. Thus, the scope of the invention should not be limited by the foregoing specification, but rather only by the scope of the claims appended hereto.

I claim:

1. A method of securing an electrode to the skin of a human body for treatment or diagnostic purposes, said method being characterized by the steps of:
    positioning a surface of the electrode in contact with a desired skin area from which, or into which electrical impulses are to be directed; and
    maintaining the electrode in its desired position by confining it within the periphery of a pliable, moldable and stretchable adhesive putty including silicone polymer conforming to the configuration of the electrode and having a peripheral region surrounding the periphery of the electrode and being secured to the skin.

2. The method of claim 1 characterized by the step of establishing contact between the electrode surface and the skin without utilizing conductive gels or other adhesive materials between the skin and said electrode surface.

3. The method in accordance with claims 1 or 2 characterized in that the putty surrounds an electrical conductor attached to and extending out of the electrode.

4. The method according to claim 1 characterized in that the putty is an organosiloxane-boron compound.

* * * * *